(12) United States Patent
Katsuki (10) Patent No.: US 9,976,168 B2
(45) Date of Patent: May 22, 2018

(54) SUBSTANCE MEASUREMENT METHOD AND MEASUREMENT DEVICE EMPLOYING ELECTROCHEMICAL BIOSENSOR

(71) Applicants: ARKRAY, Inc., Kyoto (JP); BioEngineering Laboratories, LLC, Tokyo (JP)

(72) Inventor: Koji Katsuki, Kyoto (JP)

(73) Assignees: ARKRAY, Inc., Kyoto (JP); BioEngineering Laboratories, LLC, Tokyo (JP)

( * ) Notice: Subject to any disclaimer, the term of this patent is extended or adjusted under 35 U.S.C. 154(b) by 111 days.

(21) Appl. No.: 14/910,037

(22) PCT Filed: Aug. 7, 2014

(86) PCT No.: PCT/JP2014/070885
§ 371 (c)(1),
(2) Date: Feb. 4, 2016

(87) PCT Pub. No.: WO2015/020149
PCT Pub. Date: Feb. 12, 2015

(65) Prior Publication Data
US 2016/0177365 A1    Jun. 23, 2016

(30) Foreign Application Priority Data
Aug. 7, 2013  (JP) .................................. 2013-164455

(51) Int. Cl.
*G01N 27/327*  (2006.01)
*C12Q 1/00*  (2006.01)

(52) U.S. Cl.
CPC ............. *C12Q 1/006* (2013.01); *C12Q 1/005* (2013.01); *G01N 27/3272* (2013.01); *G01N 27/3273* (2013.01)

(58) Field of Classification Search
CPC ................ G01N 27/3273; C12Q 1/001–1/005
See application file for complete search history.

(56) References Cited

U.S. PATENT DOCUMENTS

| 5,108,564 A | 4/1992 | Szuminsky et al. |
| 5,128,015 A | 7/1992 | Szuminsky et al. |

(Continued)

FOREIGN PATENT DOCUMENTS

| CN | 1571925 A | 1/2005 |
| EP | 1679508 A1 | 7/2006 |

(Continued)

OTHER PUBLICATIONS

JPO computer-generated English language translation of Inoue et al. JP 2011-203032 A Downloaded Jul. 20, 2017.*

(Continued)

*Primary Examiner* — Alexander S Noguerola
(74) *Attorney, Agent, or Firm* — Morgan, Lewis & Bockius LLP (57) ABSTRACT

A method is provided for measuring a substance using a biosensor, the method comprising:
 introducing a sample containing the substance into an electrochemical measurement cell which comprises an insulating base plate; at least two electrodes formed on the insulating base plate; and a reagent layer that is disposed on at least one of the electrodes and comprises an oxidoreductase;
 applying a voltage to the electrodes;
 detecting a charge transfer limiting current which is generated due to the transfer of electrons from the substance in the sample to the electrode; and
 determining the concentration of the substance contained in the sample based on the charge transfer limiting current.

14 Claims, 8 Drawing Sheets

Chronoamperometry

(56) References Cited

U.S. PATENT DOCUMENTS

| | | | |
|---|---|---|---|
| 5,422,246 A * | 6/1995 | Koopal | A61L 31/10 |
| | | | 204/403.1 |
| 5,942,102 A | 8/1999 | Hodges et al. | |
| 6,179,979 B1 | 1/2001 | Hodges et al. | |
| 2004/0245121 A1 | 12/2004 | Nagakawa et al. | |
| 2007/0267301 A1 | 11/2007 | Sode | |
| 2009/0008248 A1 | 1/2009 | Shimomura et al. | |
| 2009/0178935 A1 | 7/2009 | Reymond et al. | |
| 2009/0321277 A1 | 12/2009 | Heller et al. | |
| 2010/0160755 A1 | 6/2010 | Oviatt et al. | |
| 2013/0240374 A1 | 9/2013 | Sode | |
| 2014/0246335 A1 | 9/2014 | Ooe et al. | |
| 2015/0129425 A1 | 5/2015 | Tsukada et al. | |
| 2015/0192537 A1 | 7/2015 | Sekimoto | |
| 2016/0186230 A1 | 6/2016 | Kaneda | |

FOREIGN PATENT DOCUMENTS

| | | | | |
|---|---|---|---|---|
| EP | 2395348 A1 | 12/2011 | | |
| EP | 2573190 A1 | 3/2013 | | |
| JP | 05-93705 A * | 4/1993 | | G01N 27/30 |
| JP | 2009-276275 A | 11/2009 | | |
| JP | 2011-058900 A | 3/2011 | | |
| JP | 2011-203032 A * | 10/2011 | | G01N 27/416 |
| JP | 2014-006154 A | 1/2014 | | |
| JP | 2014-006155 A | 1/2014 | | |
| WO | 2010/106781 A1 | 9/2010 | | |

OTHER PUBLICATIONS

Tsujimura et al., "Novel FAD-Dependent Glucose Dehydrogenase for a Dioxygen-Insensitive Glucose Biosensor," Biosci. Biotechnol. Biochem., 70 (3), 654-659, 2006.*
JPO computer-generated English language translation of Takahashi et al. JP 05-093705 A. Downloaded Sep. 23, 2017.*
Thomas Poulos, "Heme Enzymes", Encyclopedia of Molecular Cell Biology and Molecular Medicine, 2n Edition, vol. 6, pp. 33-66.*
Extended European Search Report issued in corresponding European Patent Application No. 14833693.6 dated Mar. 24, 2017.
Extended European Search Report issued in related European Patent Application No. 15201398.3 dated May 23, 2016.
International Preliminary Report on Patentability and Written Opinion issued in corresponding International Patent Application No. PCT/JP2014/070885 dated Feb. 18, 2016.
International Search Report issued in corresponding International Patent Application No. PCT/JP2014/070885 dated Sep. 30, 2014.
Office Action issued in corresponding Chinese Patent Application No. 201480044602.5 dated Dec. 21, 2017.

* cited by examiner

SUBSTANCE MEASUREMENT METHOD AND MEASUREMENT DEVICE EMPLOYING ELECTROCHEMICAL BIOSENSOR

TECHNICAL FIELD

The present invention relates to a measuring method and a measuring apparatus using an electrochemical biosensor, for analyzing a substance to be measured such as a biological substance.

BACKGROUND ART

In a conventional electrochemical biosensor, a measuring method has been mainly used in which a voltage is applied to an electrode system and a Cottrell current resulting from the diffusion of a substance is measured. For example, Patent Document 1 describes a measuring method in which an oxidizing agent and a buffering agent are incorporated in a reaction system; a reaction is allowed to proceed until the reaction is substantially completed; and then a potential is applied between electrodes and a sample, to measure the Cottrell current. The Cottrell current, represented by the Cottrell equation (the following Equation (1)), is a current which depends on the diffusion of a substance, and is characterized by including a diffusion coefficient (D) of the substance. In terms of reaction kinetics, it can be said to be a diffusion-limiting state.

$$i = \frac{nFAC_0^0 D_0^{1/2}}{\pi^{1/2} t^{1/2}} = Kt^{-1/2} \quad (1)$$

i: Current (A)
n: Reaction electron number (eq/mol)
F: Faraday constant (96,485 C/eq)
A: Electrode surface area (cm$^2$)
CO: Concentration of 0 (mol/cm$^3$)
DO: Diffusion coefficient of 0 (cm$^2$/s)
T: Time (s)

In Patent Document 2, microelectrodes are used in the measurement of an analyte in a microfluid, and measurement conditions which depend on the diffusion coefficient (D) of the analyte are disclosed.

Further, Patent Document 3 describes the Cottrell equation and the diffusion coefficient (D), and discloses an example in which the diffusion coefficient is calculated based on an experiment.

In addition, Patent Document 4 describes a step of applying a potential between electrodes such that the potential of a working electrode determines the diffusion rate of redox species.

PRIOR ART DOCUMENTS

Patent Documents

Patent Document 1: JP 2901678 B
Patent Document 2: JP 2009-533658 A
Patent Document 3: JP 2011-58900 A
Patent Document 4: JP 3863184 B

SUMMARY OF THE INVENTION

In order for the above mentioned Cottrell current to be generated, a state in which the concentration of the substance does not change is required. In other words, it is necessary that an enzyme reaction and the like be substantially completed. Therefore, a certain period of time for the enzyme reaction to be completed has to be reserved. Further, since the Cottrell current is inversely proportional to a square root of time ($\sqrt{t}$), the current decays over time. Thus, in order to reduce the measurement variation, it is necessary to carry out the measurement in the state where the fluctuation of current is small. As a result, the period of time required until the start of the measurement is increased. On the other hand, in a microelectrode system, in which a steady-state current based on the spherical diffusion of a substance is detected and in which current does not decay overtime, the measurement sensitivity is low. Therefore, it is necessary, as disclosed in Patent Document 2 and the like, to provide a plurality of electrodes in order to increase the absolute sensitivity to form an oxidation reduction reaction cycle. In view of the above, there are potential problems in general, that, in the diffusion-limiting measurement, a longer measurement time is required, and in the measurement using a microelectrode system, it is necessary to provide a plurality of electrodes, which complicates the electrode system.

Accordingly, an object of the present invention is to provide a method and an apparatus for measuring a substance using an electrochemical biosensor, in which the measurement can be carried out with a shorter time, a higher accuracy, and a simple system.

As a result of intensive studies in order to achieve the detection of a current which is based, not on the diffusion process of a substance as in conventional methods, but on another process of electrochemical reaction, the present inventors have discovered that it is possible to measure a substance with a shorter time and with a higher accuracy by detecting a current resulting from the charge transfer process, not the diffusion process of the substance, in the measurement using an electrochemical biosensor, thereby completing the present invention.

Accordingly, the measurement method according to the present invention comprises:

introducing a sample containing a substance into an electrochemical measurement cell which comprises an insulating base plate; at least two electrodes formed on the insulating base plate; and a reagent layer that is disposed on at least one of the electrodes and comprises an oxidoreductase;

applying a voltage to the electrodes;

detecting a charge transfer limiting current which is generated due to the transfer of electrons derived from the substance in the sample to the electrode; and determining the concentration of the substance contained in the sample based on the charge transfer limiting current.

In the above mentioned method, the charge transfer limiting current is preferably a steady-state current observed after the generation of a transient current due to the charging of an electric double layer, and more preferably, represented by the following Equation (6).

Further, the oxidoreductase preferably contains pyrroloquinoline quinone or flavin adenine dinucleotide, or has a subunit or domain containing heme.

More specifically, the oxidoreductase is preferably an enzyme having a glucose oxidation activity, such as glucose dehydrogenase, and the substance to be measured is preferably glucose.

In addition, it is preferred that the voltage be applied in a stepwise manner, and the voltage to be applied is preferably 600 mV or less.

The measuring apparatus according to the present invention comprises:
  a biosensor comprising:
    an electrochemical measurement cell comprising:
      an insulating base plate;
      at least two electrodes formed on the insulating base plate; and
      a reagent layer that is disposed on at least one of the electrodes and comprises an oxidoreductase capable of reacting with a substance to be measured in a sample;
  a control section configured to control the application of voltage to the biosensor;
  a detection section configured to detect a charge transfer limiting current based on the transfer of electrons derived from the substance to the electrode, wherein the charge transfer limiting current is generated by the application of voltage to the biosensor;
  an arithmetic section configured to calculate the concentration of the substance based on the value of the charge transfer limiting current; and
  an output section configured to output the calculated concentration of the substance.

In the above mentioned measurement apparatus, the control section is preferably configured to control such that the voltage is applied in a stepwise manner. Further, in the above mentioned measuring apparatus, the substance to be measured is preferably glucose, and the oxidoreductase is preferably an enzyme having a glucose oxidation activity, such as glucose dehydrogenase.

Since the present invention allows for measuring the concentration of a substance without being affected by the diffusion thereof, the time required for measurement can be reduced. In addition, since a simple electrode system can be used, it is possible to reduce the cost. Based on these effects, it is possible to improve the operability of the measurement while requiring a less amount of specimen and a shorter measurement time, thereby improving the usability.

BRIEF DESCRIPTION OF THE DRAWINGS

FIG. 1A and FIG. 1B show the structure of biosensors of the Examples and the Comparative Example, where

EMBODIMENTS FOR CARRYING OUT THE INVENTION

An embodiment of the present invention will now be described. However, the embodiment to be described below is provided for illustrative purposes, and the present invention is not limited to the constitution of the following embodiment.

The measurement method using a biosensor according to the present invention comprises:
  introducing a sample containing a substance into an electrochemical measurement cell which comprises an insulating base plate; at least two electrodes formed on the insulating base plate; and a reagent layer that is disposed on at least one of the electrodes and comprises an oxidoreductase;
  applying a voltage to the electrodes;
  detecting a charge transfer limiting current which is generated due to the transfer of electrons derived from the substance in the sample to the electrode; and
  determining the concentration of the substance contained in the sample based on the charge transfer limiting current.

In the above mentioned method, the substance to be measured is not particularly limited as long as it can be measured by the measurement method using a biosensor according to the present invention. However, the substance to be measured is preferably a substance derived from a living body, which can serve as an index of a disease and/or health status, and examples thereof include glucose, cholesterol, and the like. The sample is not particularly limited as long as it contains the substance to be measured. However, a biological sample, such as blood or urine is preferred.

The charge transfer limiting current based on the transfer of electrons derived from the substance to be measured to the electrode is a current which is generated when the electrons are transferred from the oxidoreductase to the electrode due to the reaction between the oxidoreductase and the substance to be measured. Further, the charge transfer limiting current is a steady-state current which does not depend on time, and preferably, a steady-state current observed after the generation of a transient current due to the charging of an electric double layer.

The charge transfer limiting current is preferably represented by the following Equation (5). It can be seen from the Equation (5) that the current is proportional to the concentration of the substrate and to the enzyme reaction rate constant, and when the constant term is defined as X, it can be expanded to Equation (6). Although not shown in Equations (5) and (6), the constant term X may include a correction coefficient and/or the like.

$$i = \frac{nFAC_s^0 K_{cat'} \tau_E}{Km} \qquad (5)$$

i: Current (A)
n: Reaction electron number (eq/mol)
F: Faraday constant (96,485 C/eq)
A: Electrode surface area (cm$^2$)
$C_s^0$: Concentration of substrate (S)(mol/cm$^3$)
$\tau_E$: Amount of Enzyme (mol)
$K_{cat}$/Km: enzyme reaction rate constant $$i = X \cdot \frac{K_{cat}}{Km} \cdot C_s^0 \quad (6)$$

The present inventors have considered that in order to measure the concentration of the substance to be measured (substrate), taking the initial rate equation (Equation (2)) and the equation of the electron transfer rate from the enzyme to the electrode (Equation (3)) into the consideration, it is necessary that the current need to be detected under the conditions where the values of these equations are equal (Equation (4)). Therefore, by expanding the Equation (4) into a current equation, they have obtained Equation (5) of the charge transfer limiting current.

Equation (5) is an equation of charge transfer limiting current, which does not include the diffusion coefficient (D) included in the Cottrell current of the above mentioned Equation (1). As can be seen from Equation (5), the current is proportional to the enzyme reaction rate constant. Since in the measurement method of the present invention, electrons are transferred to the electrode without being mediated by an oxidation reduction reaction by a mediator such as an electron acceptor substance, it can be seen that the measurement is not affected by the diffusion of the substance, and it does not depend on time, either.

$$V_{(En)} = \frac{K_{cat} C_s^0 \tau_E}{Km} \quad (2)$$

$C^0_s$: Concentration of substrate (S)(mol/cm³)
$\tau_E$: Amount of Enzyme (mol)
$K_{cat}/Km$: enzyme reaction rate constant $$V(d) = \frac{i}{nFA} \quad (3)$$

i: Current (A)
n: Reaction electron number (eq/mol)
F: Faraday constant (96,485 C/eq)
A: Electrode surface area (cm²)

$$\frac{K_{cat} C_s^0 \tau_E}{Km} = \frac{i}{nFA} \quad (4)$$

It is possible to confirm if the electrode system is charge transfer limiting, by examining the presence or absence of a peak, and the pattern of current increase due to the sweep direction of the voltage, using cyclic voltammetry or the like.

The electrochemical biosensor which can be used in the measurement method according to the present invention will now be described.

<Working Electrode>

The working electrode can be obtained, for example, by disposing an electrode material on an insulating base plate to form an electrode, and by disposing a reagent layer containing at least an oxidoreductase in the vicinity of the resulting electrode.

The electrode is formed, for example, using a carbon material such as carbon. Alternatively, a metallic material such as gold (Au), platinum (Pt), silver (Ag), or palladium can also be used.

The insulating base plate is made of an insulating material, and examples thereof include various types of resins (plastics), such as thermoplastic resins, for example, polyetherimide (PEI), polyethylene terephthalate (PET) and polyethylene (PE), polyimide resins, and epoxy resins; glasses; ceramics; papers; and the like.

The size and the thickness of the electrode and the insulating base plate can be determined as appropriate.

<Oxidoreductase>

The oxidoreductase can be any enzyme capable of oxidizing and reducing the substance to be measured, and can contain at least one of pyrroloquinoline quinone (PQQ) and flavin adenine dinucleotide (FAD), as a catalytic subunit and a catalytic domain. Examples of the oxidoreductase containing PQQ include PQQ glucose dehydrogenase (PQQGDH). Examples of the oxidoreductase containing FAD include cytochrome glucose dehydrogenase (CyGDH) and glucose oxidase (GOD), having an α subunit containing FAD.

In addition, the oxidoreductase can contain an electron transfer subunit or an electron transfer domain. Examples of the electron transfer subunit include a subunit containing heme which has a function of giving and receiving electrons. Examples of the oxidoreductase having the subunit containing heme include those containing cytochrome. For example, a fusion protein of glucose dehydrogenase or PQQGDH with cytochrome can be used.

Further, examples of the enzyme containing the electron transfer domain include cholesterol oxidase and quinoheme ethanol dehydrogenase (QHEDH (PQQ Ethanol dh). As the electron transfer domain, it is preferred to use a domain containing cytochrome having heme which has a function of giving and receiving electrons. Examples thereof include "QHGDH" (fusion enzyme; GDH with heme domain of QHGDH), sorbitol dehydrogenase (Sorbitol DH), D-fructose dehydrogenase (Fructose DH), glucose-3-dehydrogenase derived from *Agrobacterium tumefasience* (G3DH from *Agrobacterium tumefasience*), and cellobiose dehydrogenase. A fusion protein of PQQGDH with cytochrome, which is an example of the above mentioned subunit containing cytochrome, and a cytochrome domain of PQQGDH, which is an example of the domain containing cytochrome, are disclosed, for example, in WO 2005/030807.

Further, as the oxidoreductase, it is preferred to use an oligomeric enzyme including at least a catalytic subunit and a subunit containing cytochrome having heme which has a function as an electron acceptor.

The substance to be measured can be any substance which serves as a substrate for oxidoreductase. For example, since cellobiose dehydrogenase oxidizes not only cellobiose but also glucose, glucose can also be used as the substance to be measured.

In order to measure the charge transfer limiting current, it is preferred that a "direct electron transfer-type enzyme electrode" be used as a working electrode. The "direct electron transfer-type enzyme electrode" as used herein refers to a type of an enzyme electrode in which electrons are transferred between the enzyme and the electrode in such a way that electrons generated by an enzyme reaction in a reagent layer are directly transferred to the electrode without the involvement of an oxidation-reduction substance, such as an electron transfer mediator.

The limiting distance within which the direct electron transfer can occur in a physiological reaction system is reported to be from 1 to 2 nm. Therefore, it is important that the molecules of the enzyme be positioned such that the transfer of electrons from the enzyme to the electrode is not interfered.

In order to measure the charge transfer limiting current, it is important that the molecules of an oxidoreductase be positioned in the vicinity of the electrode. Examples of the method therefor include: a method in which the molecules of an oxidoreductase are chemically immobilized to the electrode; a method in which the molecules of an oxidoreductase are indirectly immobilized to the electrode using a binder or the like, and a method in which the molecules of an oxidoreductase are allowed to be physically adsorbed on the electrode; but not limited thereto.

The enzyme reagent layer on the working electrode can contain electrically conductive particles. By containing electrically conductive particles, it can be expected that electrons are suitably transferred to the electrode. Specifically, particles of a metal such as gold, platinum, silver or palladium; or a higher-order structure made of a carbon material can be used, as the electrically conductive particles. The higher-order structure can contain, for example, carbon particles or carbon fine particles, such as particles of electrically conductive carbon black, carbon nanotube (CNT) or fullerene. Examples of electrically conductive carbon black include KETJENBLACK® (manufactured by Degussa Corporation), BLACK PEARLS (manufactured by Cabot Corporation) and the like.

The enzyme reagent layer on the working electrode can also contain an electrically conductive polymer. The electrically conductive polymer is preferably a water-soluble polymer, and examples thereof include polyaniline, polyethylenedioxythiophene and the like. Representative examples thereof include sulfonated polyaniline aqueous solution manufactured by Mitsubishi Rayon Co., Ltd. (AquaPASS®).

The enzyme reagent layer on the working electrode can also contain a binder. The binder is preferably a water soluble binder, and specific examples thereof include an oxazoline group-containing water soluble polymer and the like.

The above mentioned working electrode can be prepared, for example, as follows. Specifically, a carbon layer which functions as an electrode is formed on one surface of an insulating base plate. For example, a carbon film having a desired thickness (for example, about 10 µm) can be prepared by screen printing a carbon ink on one surface of the insulating base plate in the form of a film having a predetermined thickness (for example, about 100 µm). Instead of the carbon layer, it is also possible to form a metal layer having a desired thickness (for example, about 30 nm) by depositing a metallic material with physical vapor deposition (PVD, for example by sputtering), or with chemical vapor deposition (CVD).

Next, an enzyme reagent layer is formed on the electrode. First, a solution containing an oxidoreductase, electrically conductive particles, and an electrically conductive polymer is prepared, and the resulting solution is dropped on the surface of the electrode. Then the solution is allowed to dry and solidify on the electrode, to obtain a working electrode in which an enzyme reagent layer is formed on top of the electrode.

As a counter electrode, it is possible to use any electrode which can be generally used as the counter electrode in a biosensor. Examples thereof include: a carbon electrode prepared in the form of a film by screen printing; a metal electrode prepared in the form of a film by physical vapor deposition (PVD, for example, sputtering) or chemical vapor deposition (CVD); and a silver/silver chloride electrode prepared in the form of a film by screen printing. It is also possible to employ a 3-electrode system in which silver/silver chloride electrode is used as a reference electrode.

There is no particular limitation on the manner in which a voltage is applied to the electrodes. However, in order to efficiently measure the charge transfer limiting current, a stepwise application is preferred. The voltage to be applied is preferably 600 mV or less, more preferably, 100 mV or less. The lower limit of the voltage to be applied is not particularly limited, but it is 10 mV or more, for example.

The concentration of the substance to be measured can be calculated from the measured current value based on Equation (5).

It is also possible to prepare a calibration curve in advance, using a sample having a known concentration, and to calculate the concentration from the measured current value, based on the calibration curve. In addition, the concentration of the specimen can also be calculated by multiplying a correction coefficient obtained by a test to Equation (5), and the like. In this case, the correction coefficient is included in the constant term X in Equation (6).

According to the measurement method of the present invention, the measurement can be carried out either continuously or intermittently.

Next, the measuring apparatus according to the present invention will be described with reference to the drawings. However, the measuring apparatus of the present invention is not limited to the following aspects.

Figure 7:
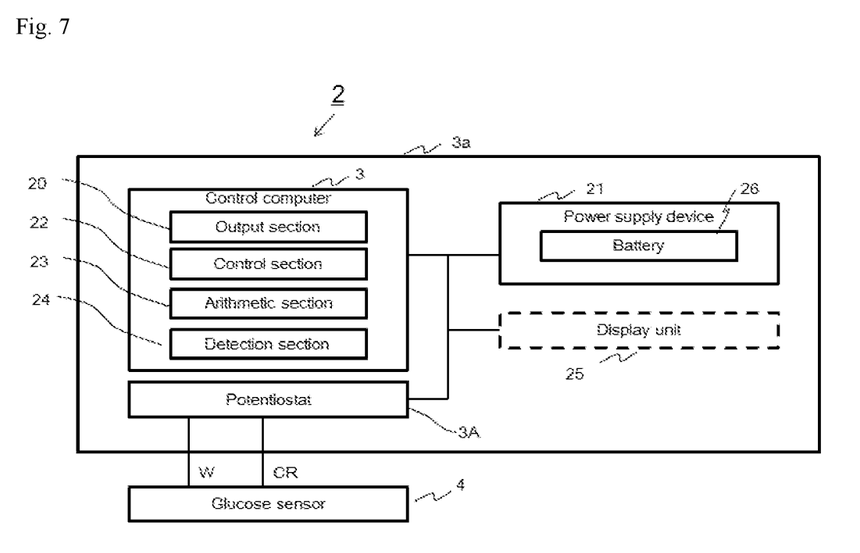
FIG. 7 is a schematic diagram illustrating one aspect of a measuring apparatus according to the present invention.

FIG. 7 shows an example of the configuration of main electronic components included in a measuring apparatus 2. A control computer 3, a potentiostat 3A and a power supply device 21, as shown in FIG. 7, are provided on a base plate 3a housed in a housing.

The control computer 3 include, as hardware, a processor such as CPU (central processing unit); a recording medium such as a memory (RAM (Random Access Memory) or ROM (Read Only Memory)); and a communication unit. When the processor loads a program stored in the recording medium (for example, the ROM) to the RAM, and executes the program, the control computer 3 functions as an apparatus including an output section 20, a control section 22, an arithmetic section 23 and a detection section 24. The control computer 3 may also include an auxiliary memory such as a semiconductor memory (EEPROM or flash memory) or a hard disk.

The control section 22 controls the timing for applying the voltage and the value of the voltage to be applied, and the like.

The power supply device 21 includes a battery 26, and supplies electricity to the control computer 3 and the potentiostat 3A for operation. It is also possible to dispose the power supply device 21 outside the housing.

The potentiostat 3A is a device which maintains the potential of the working electrode constant with respect to the potential of the reference electrode. The potentiostat 3A, which is controlled by the control section 22, applies a predetermined amount of voltage, in a stepwise manner, between the counter electrode and the working electrode of the glucose sensor 4 using terminals CR and W; measures the response current of the working electrode which can be obtained at the terminal W; and send the result of the measurement to the detection section 24.

The arithmetic section 23 calculates the concentration of the substance to be measured based on the value of the detected current, and stores the calculated result. The output section 20 carries out data communication between the output section 20 and the display section unit 25, and sends the calculated result of the concentration of the substance to be measured provided by the arithmetic section 23 to the display section unit 25. The display section unit 25 is capable of displaying, for example, the calculated result of the glucose concentration which is received from the measuring apparatus 2, on a display screen in a predetermined format.

Figure 8:
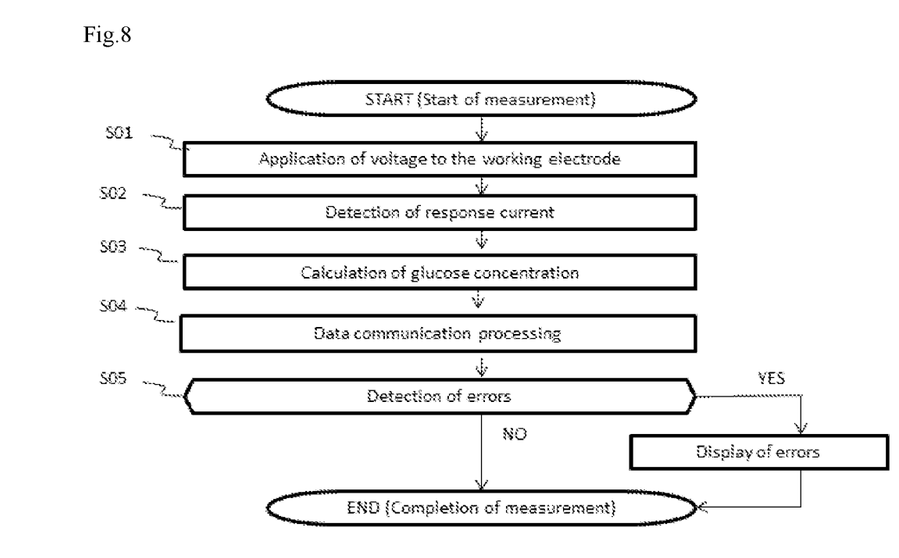
FIG. 8 is a flow chart illustrating one aspect of a measurement program using the measuring apparatus according to the present invention.

FIG. 8 is a flow chart showing an example of the processing sequence of the glucose concentration measurement carried out by the control computer 3.

In FIG. 8, when the CPU (control section 22) of the control computer 3 receives an instruction to start the measurement of the glucose concentration, the control section 22 controls the potentiostat 3A to apply a predetermined amount of voltage to the working electrode in a stepwise manner, and starts measuring the response current from the working electrode (Step S01). Further, the detection of the installation of a sensor to the measuring apparatus may be used as the instruction to start the measurement of the concentration.

Next, the potentiostat 3A measures the response current generated by the application of voltage, specifically, the charge transfer limiting current based on the transfer of electrons derived from the substance to be measured (glucose, in this embodiment) in the sample to the electrode, preferably, the steady-state current observed after the occurrence of the transient current due to the charging of an electric double layer, for example, the steady-state current observed 1 to 20 seconds after the application of voltage. Then, the potentiostat 3A sends the measured current to the detection section 24 (Step S02).

The arithmetic section 23 carries out arithmetic processing based on the measured current value, and calculates the glucose concentration (Step S03). For example, the equation (based on the above described Equation (5) or (6)) for calculating the glucose concentration or the data of the calibration curve of the glucose concentration, which corresponds to the glucose dehydrogenase placed on the electrode, is preinstalled to the arithmetic section 23 in the control computer 3, and the arithmetic section 23 calculates the glucose concentration utilizing these calculation equation or the calibration curve.

The output section 20 sends the calculated result of the glucose concentration to the display section unit 25, through a communication link provided between the output section 20 and the display section unit 25 (Step S04). Thereafter, the control section 22 determines if there are any measurement errors detected (Step S05); completes the measurement if there is no error; and displays the glucose concentration on the display section. If there are any errors, a notification of error is displayed, and then the flow sequence shown in FIG. 8 is completed. Further, the calculated result can be stored in the arithmetic section 23, so that the stored result can be reloaded afterwards to be displayed on the display section for confirmation. Although the detection of measurement errors by the control section 22 (Step S05) is carried out after the calculated result is sent to the display section unit 25 (Step S04) in this embodiment, it is also possible to carry out these steps in different orders.

The present invention will now be more specifically described referring to Examples. However, the present invention is not limited to the aspects of the following Examples.

Example 1

Examples of the biosensor will now be described using a glucose sensor.

<Production Method of Glucose Sensor>

Figure 1A:
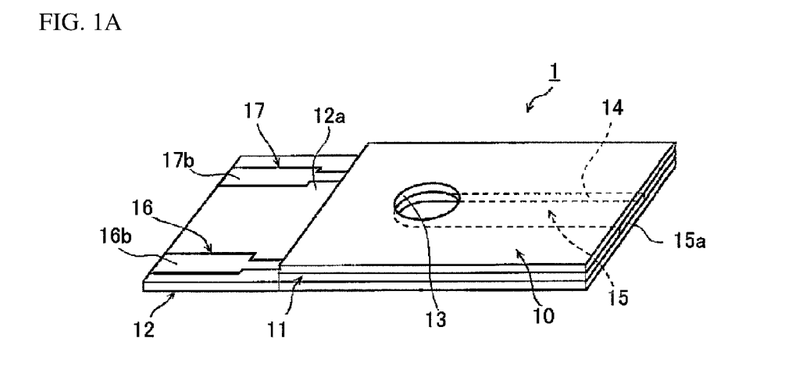
FIG. 1A is an overall perspective view thereof.
Figure 1B:
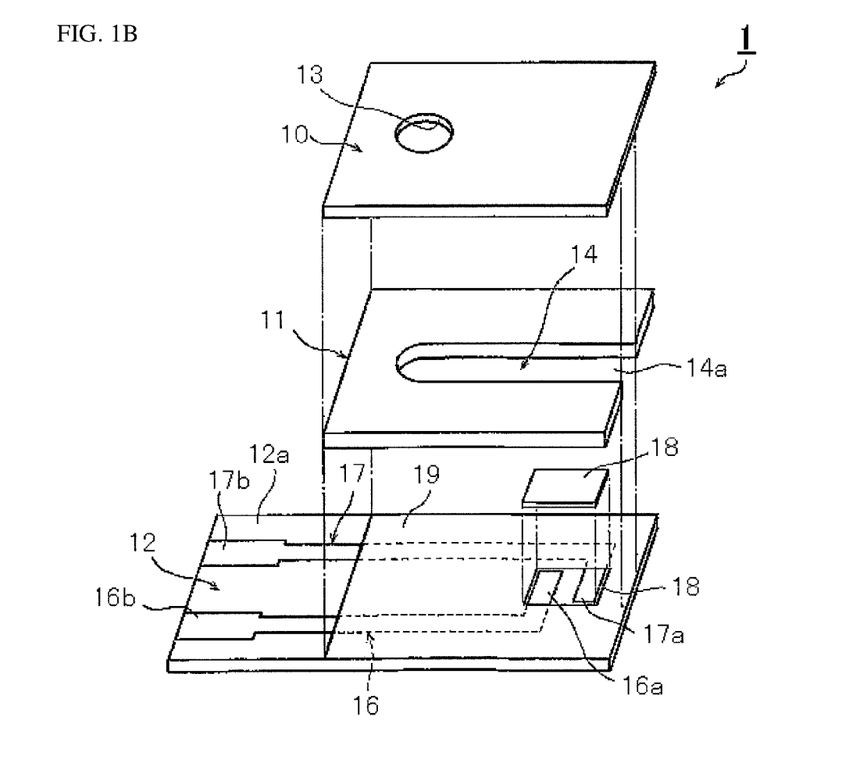
FIG. 1B is an exploded perspective view thereof.

FIG. 1A and FIG. 1B show an example of the glucose sensor.

As shown in FIG. 1A and FIG. 1B, the glucose sensor 1 includes a cover plate 10, a spacer 11, and a base plate 12.

The cover plate 10 is provided with a hole 13, and the spacer 11 is provided with a slit 14 having a narrow width, which communicates with the hole 13 and opens at a distal end portion 14a. In the state where the cover plate 10 and the spacer 11 are laminated on an upper surface 12a of the base plate 12, such that the spacer 11 is sandwiched between the base plate 12 and the cover plate 10, the slit 14 defines a capillary 15. The capillary 15 communicates with the exterior of the glucose sensor through a distal end opening 14a of the slit 14 and the hole 13. The distal end opening 14a defines a sample liquid introduction port 15a, and the sample liquid supplied through the sample liquid introduction port 15a moves within the capillary 15 toward the hole 13 due to the capillary phenomenon.

A first electrode 16, a second electrode 17, and a reagent layer 18 are provided on the upper surface 12a of the base plate 12.

Overall, the first and the second electrodes 16 and 17 extend in the longitudinal direction of the base plate 12, and end portions 16a and 17a of the electrodes extend in the width direction of the base plate 12. The upper surface 12a of the base plate 12 is covered by an insulating film 19 such that the end portions 16a, 16b, 17a, and 17b of the first and the second electrodes 16 and 17 are exposed.

The reagent layer 18 is disposed so as to bridge between the end portions 16a and 17a of the first and the second electrodes 16 and 17. The reagent layer 18 contains glucose dehydrogenase.

More specifically, the glucose sensor is produced according to the following method.

<Base Electrode>

As the base electrode material, an electrically conductive carbon ink (FTU series; manufactured by Asahi Chemical Research Laboratory Co., Ltd.) was used, and this ink was pattern printed on one surface of a polyethylene terephthalate base material (E-22; manufactured by Toray Industries, Inc.) (length: 50 mm, width: 5 mm, thickness: 250 µm) to form a 2-electrode pattern. Further, in Examples, a silver/silver chloride ink (manufactured by BAS Inc.) was coated on one of the electrodes, and dried at 80° C. for 20 minutes, to form a silver/silver chloride electrode to be used as a counter electrode.

Next, an insulation resin polyester ink (UVF series; manufactured by Asahi Chemical Research Laboratory Co., Ltd.) was printed on the electrodes by screen printing. Each of the surface area of the electrodes defined by the electrode pattern and insulation pattern is determined to be 0.5 $mm^2$.

Formation of Enzyme Reagent Layer (Examples 1 and 2)

An enzyme reagent containing cytochrome-containing glucose dehydrogenase (CyGDH), electrically conductive particles (carbon black: KETJENBLACK® KJB), an electrically conductive polymer (polyaniline) as a conductive auxiliary agent, and a binder (oxazoline group-containing water soluble polymer) was prepared, and 0.04 µL of the resulting solution was dropped on the electrodes and dried at 100° C. for 30 minutes to prepare an enzyme reagent layer. The final concentration of the enzyme reagent is as follows.

<Composition of the Enzyme Reagent>
  KJB: 0.4 wt %
  Enzyme (CyGDH): 7 mg/mL
  Sodium phosphate buffer solution: 10 mM, pH 7
  Binder (EPOCROS™ WS-700; manufactured by NIPPON SHOKUBAI Co., Ltd.): 5.0% (w/v)
  Polyaniline (AquaPASS® manufactured by Mitsubishi Rayon Co., Ltd.): 0.2% (w/v)

The composition of the enzyme reagent used in Example 2 was the same as that in Example 1, except that distilled water was added instead of polyaniline.

Formation of Enzyme Reagent Layer (Example 3)

Instead of CyGDH, QHGDH (a fusion protein of PQQGDH and cytochrome) which contains cytochrome and is derived from PQQGDH was used.

The enzyme reagent having the following composition was prepared, and 0.08 µL of the resulting reagent was dropped on the electrodes and dried at 100° C. for 2 hours to form an enzyme reagent layer.

<Composition of the Enzyme Reagent>
  Lion paste (W-311N; containing KETJENBLACK®) (manufactured by Lion Corporation): 2.4 wt %
  Enzyme (QHGDH): 2.3 mg/mL
  HEPES buffer solution: 20 mM, pH 7
  Binder (EPOCROS™ WS-700; manufactured by NIPPON SHOKUBAI Co., Ltd.): 6.0% (w/v)
  Polyaniline (AquaPASS®; manufactured by Mitsubishi Rayon Co., Ltd.): 0.4% (w/v)

Comparative Example

Formation of Enzyme Reagent Layer (Comparative Example)

An enzyme reagent (first reagent) containing an electron acceptor substance (ruthenium amine complex) and an inorganic gel (smectite) as a binder was prepared, and 0.3 µL of the resulting reagent was dropped on the electrodes, and dried at 30° C. for 10 minutes, to form a first reagent layer. The final concentration of the first reagent is as follows.

<Composition of the First Reagent>
  Smectite (SWN; manufactured by Co-op Chemical Co., Ltd.): 0.3% (w/v)
  [Ru(NH$_3$)$_6$]Cl$_3$ (manufactured by Sigma-Aldrich®): 5.0% (w/v)

Next, 10 µL of an aqueous solution containing 5000 U/mL of cytochrome-containing glucose dehydrogenase (CyGDH or QHGDH) was dispensed on the first reagent layer and dried at 30° C. for 10 minutes, to form an enzyme reagent layer. In Comparative Example, carbon electrodes prepared in the same manner as in Example 1 were used as the base electrodes, to be used as the working electrode and the counter electrode.

<Formation of Capillary>

In each of the glucose sensors of Examples 1, 2 and 3, and Comparative Example, the capillary was formed as follows.

Onto the above described base electrodes on top of which the enzyme reagent layer was formed, the spacer provided with an opening was disposed, such that the spacer was placed on top of the insulating layer covering the electrodes. Further, the cover provided with a through-hole which serve as an air hole is further disposed on top of the spacer, to provide a glucose sensor. The space defined by the opening of the spacer, which is sandwiched between the cover and the insulating layer, serves as a capillary structure, and thus it is defined as a sample supplying portion.

<Cyclic Voltammetry Measurement>

Figure 2:
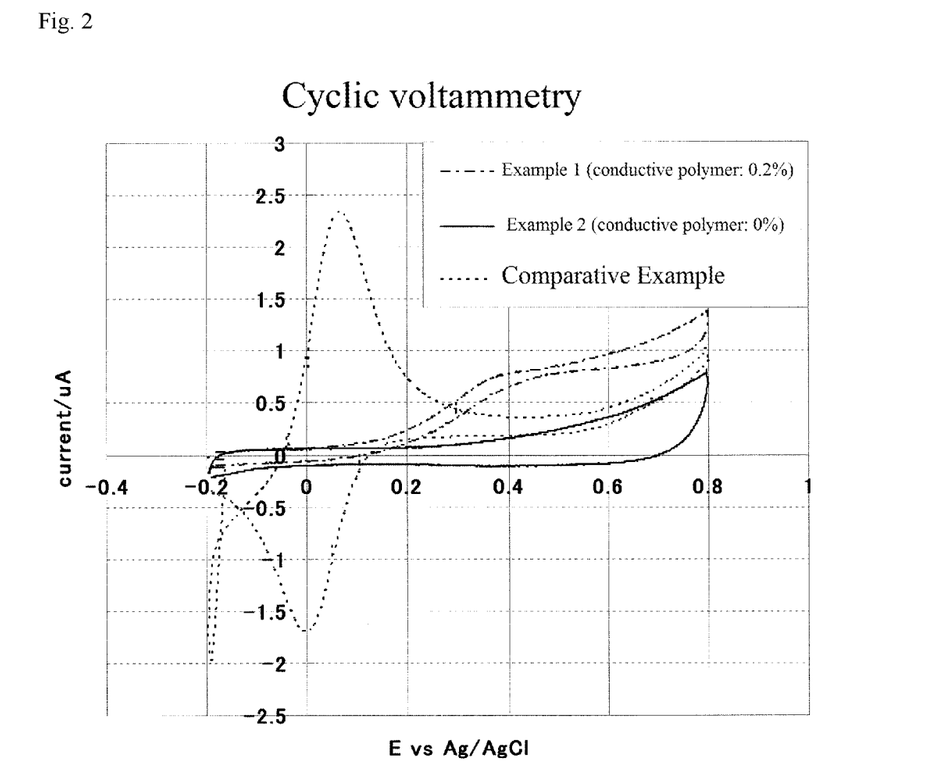
FIG. 2 is a graph showing the results of a cyclic voltammetry measurement carried out using the biosensors of Examples 1 and 2, and the Comparative Example.

The cyclic voltammetry waveforms of the glucose sensors of Examples 1 and 2, and Comparative Example were examined to evaluate the electrode response characteristics of the glucose sensors. Each of the cyclic voltammetry waveforms was obtained as follows: a whole blood sample having a glucose concentration of 100 mg/dL was introduced into the sample supplying portion of the glucose sensor, then the voltage was swept from −200 mV to +800 mV, and then to −200 mV, at a sweep rate of 20 mV/sec, and the response current during the sweeping was measured. FIG. 2 shows the cyclic voltammetry waveforms obtained by the measurement.

In the cyclic voltammetry measurement, in cases where the electrode system is diffusion-limiting, firstly, the current is increased as the rate of electrode reaction is increased, and then the current is decreased when the current becomes diffusion-dependent, and as a result, a peak is observed. The waveform of Comparative Example shows a distinct peak characteristic of diffusion limiting. However, no definite peak can be observed in the results of Example 1 and Example 2, and a tendency for a mild increase is observed. This confirms that the current detected with each of the biosensors of the present invention is a charge transfer limiting current, not a diffusion limiting current. In addition, since no peak was observed regardless of the presence of the electrically conductive polymer in the enzyme reagent layer, it can be considered that the electrically conductive polymer is not a factor responsible for altering the limiting process of the electrode system. Accordingly, the electrically conductive polymer may or may not be used in order to detect the charge transfer limiting current. However, since higher current values were observed with the biosensor of Example 1, provided with an enzyme reagent layer containing an electrically conductive polymer, it can be seen that the electrically conductive polymer has an effect of improving the response sensitivity. The above results show that the charge transfer limiting current can be detected with both the biosensors of Examples 1 and 2, and that the biosensor of Example 2 causes no inconvenience in the measurement. In the following tests, evaluation was carried out using the biosensor of Example 1 as a representative example.

<Chronoamperometry Measurement>

The electrode response characteristics of the glucose sensor were evaluated by chronoamperometry measurement. The chronoamperometry measurement was carried out as follows: a whole blood sample having a glucose concentration of 100 mg/dL was introduced into the sample supplying portion of the glucose sensor, then a voltage of 400 mV was applied to the working electrode in a stepwise manner, and the response current was measured.

Figure 3:
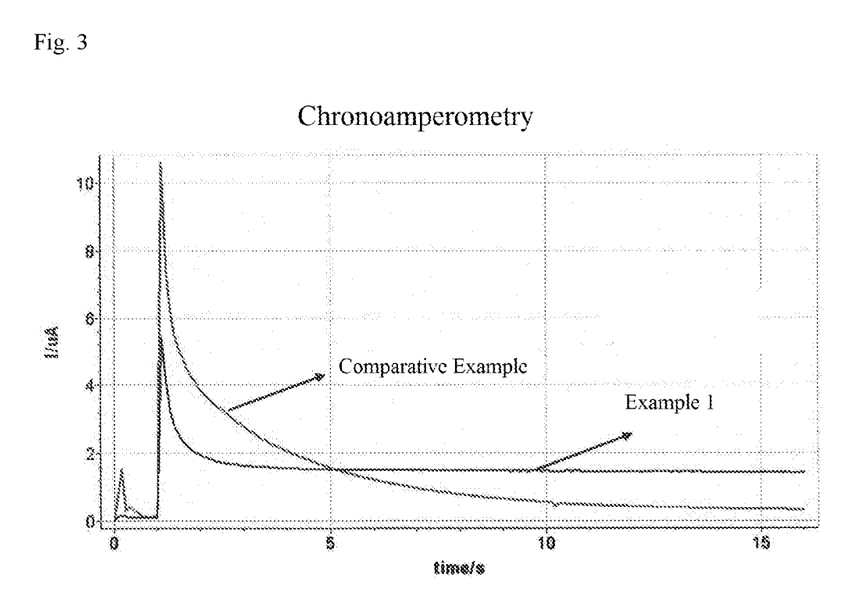
FIG. 3 is a graph showing the results of a chronoamperometry measurement carried out using the biosensors of Example 1 and the Comparative Example.
Figure 4A:
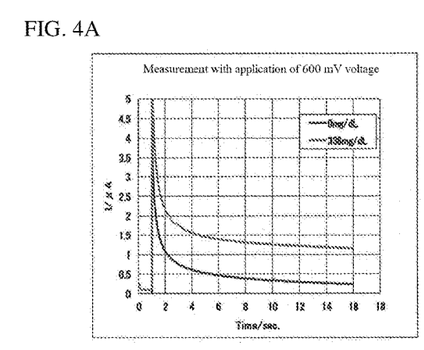
FIGS. 4A through 4E show graphs illustrating the results of the chronoamperometry measurement carried out using the biosensor of Example 1, with varying voltage parameters.
Figure 4B:
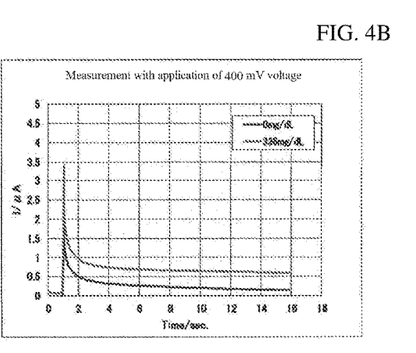
Figure 4C:
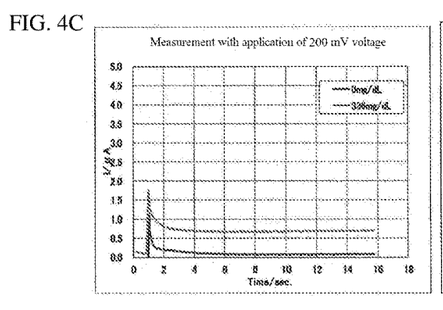
Figure 4D:
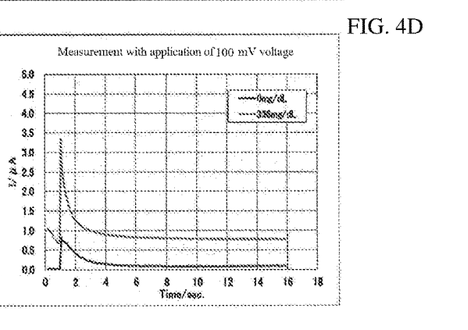
Figure 4E:
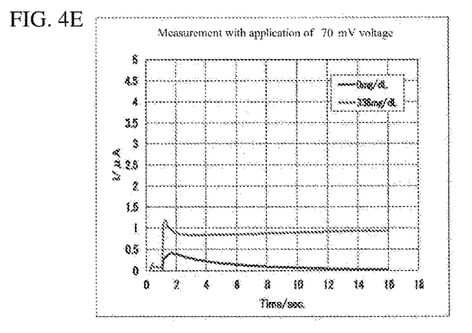

The chronoamperometry measurement was carried out using the biosensors produced as described above, and the results are shown in FIG. 3. In each of Example 1 and Comparative Example, a transient current is observed after the application of voltage. This is a current generated due to the charging of electric double layer of the electrode surface. The electric double layer is a layer generated due to the arrangement of electrolyte ions in order to maintain electrical neutrality, at the interface of the electrode surface and a solution, on the side of the solution. When the biosensor of Comparative Example was used, it was confirmed that, after the generation of the charging current, the diffusion-limiting Cottrell current is decreased at a rate of $1/\sqrt{t}$ based on Equation (1). On the other hand, when the biosensor of Example 1 was used, even though a microelectrode system was not used therein, the steady-state current was detected immediately after the generation of charging current, and by measuring this steady-state current, the glucose concentration can be measured. Thus, it was confirmed that the current measured using the biosensor of the present Example was charge transfer-limited, not diffusion-limited, and that the measurement can be achieved in a shorter time as compared to the diffusion-limited measurement.

<Chronoamperometry Measurement (Voltage Parameter)>

The electrode response characteristics of the glucose sensor of Example 1 were evaluated by chronoamperometry measurement. The chronoamperometry measurement was carried out as follows: a whole blood sample having a glucose concentration of 0 mg/dL or 336 mg/dL was introduced into the sample supplying portion of the glucose sensor, then a step voltage was applied to the working electrode, and the response current 10 seconds after the application of voltage was measured. The measuring voltage was varied in five levels of 600, 400, 200, 100, and 70 mV.

The chronoamperometry measurement was carried out using the biosensor prepared as described above, and the results are shown in FIGS. 4A through 4E. For the sample having a glucose concentration of 336 mg/dL, a similar level of steady-state current response limited by charge transfer was observed at each of the voltages. Further, since the current value of the sample having a glucose concentration of 0 mg/dL was low, it was confirmed that the measurement of glucose is possible at each of the measuring voltages. In this measurement, the current value was measured 10 seconds after the application of the step voltage. However, the results shown in FIGS. 4A through 4E show that the steady-state current was detected about 1 to 2 seconds after the application of the step voltage, and particularly, at the low voltage of 70 mV, the steady-state current was detected within one second. This confirms that the measurement can be carried out within a short period of time. As can be seen from FIGS. 4A through 4E, since reducing the amount of voltage applied allows for reducing the background current due to the oxidation reduction reaction of a coexisting substance(s) contained in the sample, it has an effect of reducing not only the time required for the measurement, but also the measurement errors.

Chronoamperometry Measurement: Example 3

The electrode response characteristics of a glucose sensor using QHGDH were evaluated by the chronoamperometry measurement. The chronoamperometry measurement was carried out as follows: a whole blood sample having a glucose concentration of 0 mg/dL or 600 mg/dL was introduced into the sample supplying portion of the glucose sensor, then a voltage of 200 mV was applied to the working electrode in a stepwise manner, and the response current was measured.

Figure 5:
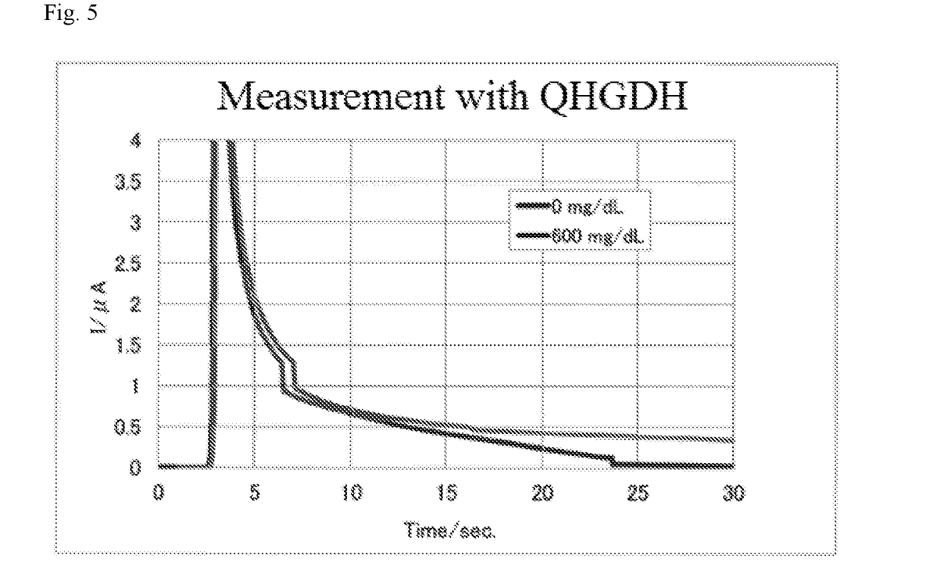
FIG. 5 is a graph showing the results of the chronoamperometry measurement carried out using the biosensor of Example 3.

The results are shown in FIG. 5. For the sample having a glucose concentration of 600 mg/dL, a steady-state current response limited by charge transfer was confirmed. On the other hand, since the current value of the sample having a glucose concentration of 0 mg/dL was low, and it was not a steady-state current response, it was found that the biosensor prepared using QHGDH containing cytochrome can also be used to measure the glucose concentration based on the steady-state current response of glucose limited by charge transfer. The reason for the fact that the steady-state current response limited by charge transfer was detected at about 15 seconds after the start of the measurement is considered to be due to the influence of the degree of purification of the enzyme and the like.

<Verification of Theoretical Equation>

Figure 6:
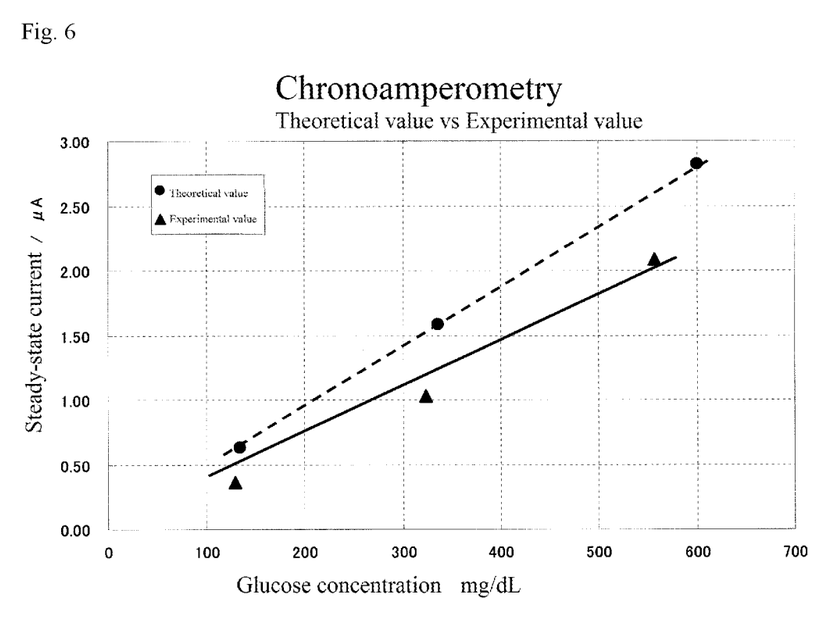
FIG. 6 is a graph obtained by plotting the values of charge transfer limiting steady-state current measured in each of the samples having varying glucose concentrations using the biosensor of Example 1, against the theoretical values of the steady-state current of each of the samples having varying glucose concentrations calculated according to theoretical Equation (5).

The value of the charge transfer limiting steady-state current of each of the samples with varying glucose concentration, which was measured 10 seconds after the application of a 70 mV step voltage to the biosensor of Example 1, was compared with the theoretical value of the steady-state current of each of the samples with varying glucose concentration calculated according to the theoretical equation: Equation (5) under the conditions as shown in Table 1 (FIG. 6).

It can be seen that the calculated values (theoretical values) correspond well with the measured values. It is possible to improve the degree of correspondence between the calculated value (theoretical value) and the measured value, by, for example, determining a correction coefficient from the deviation between the theoretical value and the measured value, and by multiplying Equation (5) with the obtained correction coefficient. Here, although the current value was measured 10 seconds after the application of the step voltage in the present measurement method, it is of course possible to measure the steady-state current about 1 to 2 seconds after the application of the step voltage.

TABLE 1

| | |
|---|---|
| n | 2 |
| F | 96485 |
| A | 0.005 |
| τ | 2.40E−12 |
| Kcat | 180 |
| Km | 0.000005 |

DESCRIPTION OF SYMBOLS

1 glucose sensor
10 cover plate
11 spacer
12 base plate
13 hole
14 slit
15 capillary
16 first electrode
17 second electrode
18 reagent layer
19 insulating film
2 measuring apparatus
20 output section
21 power supply device
22 control section
23 arithmetic section
24 detection section
25 display section unit
26 battery
3 control computer
3A potentiostat
3a base plate
CR, W terminals
4 glucose sensor

What is claimed is:

1. A method for measuring a substance using a biosensor, the method comprising:
   introducing a sample containing the substance into an electrochemical measurement cell which comprises an insulating base plate; at least two electrodes formed on the insulating base plate; and a reagent layer that is disposed on at least one of the electrodes, where the reagent layer comprises an oxidoreductase containing an electron transfer subunit or an electron transfer domain;

applying a voltage to the electrodes;

detecting a charge transfer limiting current generated from direct transfer of electrons from the oxidoreductase to the electrode as a result of reaction between the oxidoreductase and the substance; and determining concentration of the substance based on the charge transfer limiting current, wherein the charge transfer limiting current is a steady-state current observed after generation of a transient current due to charging of an electric double layer.

2. The method according to claim 1, wherein the current i is represented by the following Equation (6):

$$i = X \cdot \frac{K_{cat}}{Km} \cdot C_s^0 \qquad (6)$$

wherein:

$C_s^0$ is concentration of substrate (S) (mol/cm$^3$);

Kcat/Km is enzyme reaction rate constant; and

X is a constant term.

3. The method according to claim 1, wherein the oxidoreductase comprises pyrroloquinoline quinone or flavin adenine dinucleotide.

4. The method according to claim 1, wherein the electron transfer subunit or the electron transfer domain of the oxidoreductase contains heme.

5. The method according to claim 1, wherein the oxidoreductase has glucose oxidation activity.

6. The method according to claim 1, wherein the oxidoreductase is glucose dehydrogenase.

7. The method according to claim 1, wherein the voltage is applied in a stepwise manner.

8. The method according to claim 7, wherein the voltage is 600 mV or less.

9. The method according to claim 1, wherein the reagent layer comprises an electrically conductive polymer.

10. The method according to claim 1, wherein the substance is selected from the group consisting of glucose, cholesterol, ethanol, sorbitol, D-fructose and cellobiose.

11. The method according to claim 1, wherein the sample is a biological sample selected from the group consisting of blood and urine.

12. A measuring apparatus comprising:

a biosensor comprising:
an electrochemical measurement cell comprising:
an insulating base plate;
at least two electrodes formed on the insulating base plate; and
a reagent layer that is disposed on at least one of the electrodes, the reagent layer comprising an oxidoreductase capable of reacting with a substance to be measured in a sample, the oxidoreductase containing an electron transfer subunit or an electron transfer domain;

a control section configured to control application of voltage to the biosensor;

a detection section configured to detect a charge transfer limiting current based on direct transfer of electrons from the oxidoreductase to the electrode as a result of reaction between the oxidoreductase and the substance, wherein the charge transfer limiting current is generated by application of the voltage to the biosensor and is a steady-state current observed alter e generation of a transient current due to charging of an electric double layer;

an arithmetic section configured to calculate the concentration of the substance based on the charge transfer limiting current value; and an output section configured to output calculated concentration of the substance.

13. The measuring apparatus according to claim 12, wherein the voltage is applied in a stepwise manner due to the control section.

14. The measuring apparatus according to claim 12, wherein the substance is glucose and the oxidoreductase is glucose dehydrogenase.

* * * * *